United States Patent [19]

Fox

[11] 4,130,393
[45] Dec. 19, 1978

[54] METHOD FOR STERILIZING WITH AND RECYCLING OF ETHYLENE OXIDE

[75] Inventor: Lester A. Fox, Augusta, Ga.

[73] Assignee: Colgate-Palmolive Company, New York, N.Y.

[21] Appl. No.: 809,931

[22] Filed: Jun. 24, 1977

[51] Int. Cl.$^2$ .......................... A61L 1/00; A61L 13/00
[52] U.S. Cl. ........................................... 422/31; 422/34
[58] Field of Search ............................... 21/58, DIG. 4

[56] References Cited

U.S. PATENT DOCUMENTS

| | | | |
|---|---|---|---|
| 3,238,096 | 3/1966 | Kaye | 21/DIG. 4 |
| 3,372,980 | 3/1968 | Satas | 21/DIG. 4 |
| 3,549,312 | 12/1970 | Ernst | 21/DIG. 4 |
| 3,767,362 | 10/1973 | Griffin et al. | 21/DIG. 4 |
| 3,791,424 | 2/1974 | Strople et al. | 21/DIG. 4 |

*Primary Examiner*—Morris O. Wolk
*Assistant Examiner*—Bradley R. Garris

[57] ABSTRACT

A method of sterilizing with a mixture of ethylene oxide gas and an inert gas which makes possible reuse of the ethylene oxide for an indefinite number of successive sterilization cycles. The gas mixture is refortified with ethylene oxide when necessary. A portion of it is periodically vented when the increasing proportion of air produces a mixture which approaches the region of flammability of the mixture and is replaced with the inert gas to reduce the proportion of air in the mixture.

3 Claims, 2 Drawing Figures

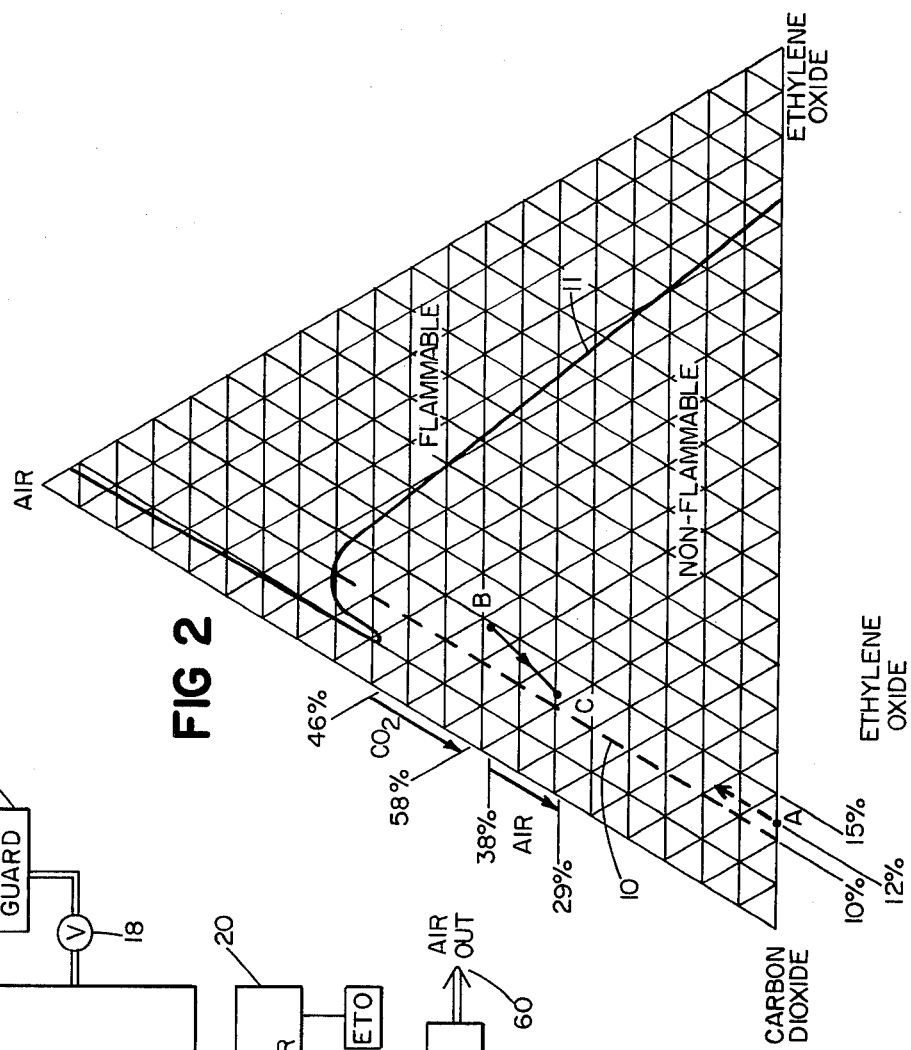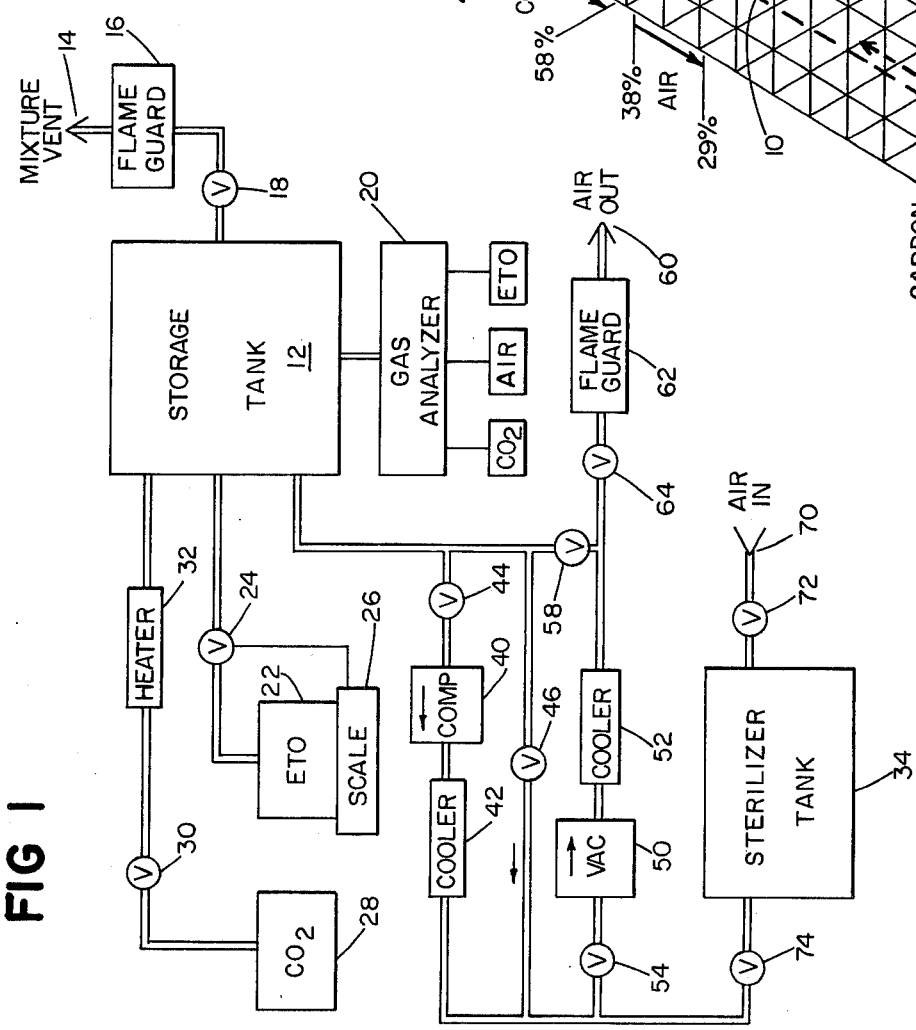

METHOD FOR STERILIZING WITH AND RECYCLING OF ETHYLENE OXIDE

BACKGROUND OF THE INVENTION

This invention relates to sterilizing with a mixture of ethylene oxide and an inert gas and, more specifically, to the use of such mixture for an indefinite number of successive sterilization cycles.

Ethylene oxide gas is widely used as a sterilizing agent in spite of its known problems of flammability, as described in *Industrial and Engineering Chemistry,* June 1950, at pages 1251–1258. For this reason, it is usually mixed with an inert gas, such as carbon dioxide, nitrogen or one of the halogenated hydrocarbons, in a proportion of about 10% to perhaps 30% of ethylene oxide.

By reason of the cost of such gas mixtures, it is desirable to reuse them for as many cycles as possible, as is discussed in Satus U.S. Pat. No. 3,372,980; Ernst U.S. Pat. No. 3,549,312 and Skocypec et al U.S. Pat. No. 3,989,461.

However, with multiple sterilization cycles, the mixture acquires a small amount of air each time it is reused, so that the increasing proportion of air in the mixture after a number of reuse cycles produces a mixture which approaches the region of flammability. Satus solves the problem by venting the entire mixture before reaching the region of flammability and replacing it with an air-free mixture. Although this is effective from the standpoint of safety, it is expensive in its utilization of gas mixtures. Ernst and Skocypec et al both use flourinated hydrocarbons as their inert gas and recondense the ethylene oxide and inert gas for reuse, the air being separated during the condensation. These systems have the disadvantage of necessitating the use of relatively expensive inert gases which can be condensed to a liquid at relatively high temperatures. They are not economically feasible for low temperature condensing gases such as carbon dioxide and nitrogen which cannot be so readily condensed.

It is accordingly a major object of the present invention to provide a method for reuse of a mixture of ethylene oxide and an inert gas for an indefinite number of successive sterilization cycles without condensing the mixture.

It is another object of the invention to decrease the cost of gas sterilization.

It is still another object of the invention to provide for effective mixing of ethylene oxide and carbon dioxide.

SUMMARY OF THE INVENTION

In one aspect of the invention, there is provided, in a method of sterilizing successive loads with ethylene oxide gas comprising using a non-flammable gas mixture containing an inert gas and at least 10% ethylene oxide gas, sterilizing loads in succession in a sterilizing tank, reusing the mixture by recirculating it to a storage tank while continuously maintaining it as a gas and refortifying it by the addition of substantially pure ethylene oxide so that the proportion of ethylene oxide initially present in the mixture sterilizing each load is at least 10%, the mixture acquiring a small amount of air during each sterilization cycle for which it is used, the refortification with ethylene oxide and the acquisition of air resulting in the mixture used for each successive load being characterized by a proportion at least 10% ethylene oxide, a decreasing proportion of inert gas and an increasing proportion of air, that improvement which comprises: periodically venting only a proportional fraction of the mixture when the increasing proportion of air in the mixture produces a mixture which approaches the region of flammability of the mixture and thereafter increasing the proportion of inert gas in the mixture to reduce the proportion of air in it while retaining the proportion of ethylene oxide at least as great as 10%, whereby an indefinite number of successive loads may be sterilized without entering the region of flammability of the mixture.

In another aspect, the present invention provides a method of mixing ethylene oxide and an inert gas, preferably carbon dioxide, to provide a uniform gaseous mixture of predetermined proportions having at least 10% ethylene oxide, comprising: first introducing a predetermined quantity of ethylene oxide from a liquid source thereof into an enclosed container, providing a source of inert gas, removing the inert gas from its source, heating it, preferably to a temperature of at least 200° F., and introducing it into the container.

The above and still further objects and features of the present invention will be apparent from the following detailed description of a preferred embodiment thereof, taken together with the accompanying drawing.

BRIEF DESCRIPTION OF THE DRAWINGS

FIG. 1 is a schematic drawing of a sterilization system useful in the practice of the present invention, and FIG. 2 is a ternary diagram of mixtures of ethylene oxide, carbon dioxide and air, showing its flammable and nonflammable regions and certain other aspects of the present invention.

DETAILED DESCRIPTION

In the system of FIG. 1 is shown an enclosed storage tank 12 having a mixture vent 14 protected by a flame guard 16 and controlled by a vent valve 18. Storage tank 12 is provided with a gas analyser 20 providing indications of the proportions of ethylene oxide, carbon dioxide and air in storage tank 12. A source of liquid ethylene oxide 22 is connected to storage tank 12 through ethylene oxide valve 24. Valve 24 may be operated by a preset scale 26 so that a predetermined quantity of ethylene oxide may automatically be introduced into storage tank 12. A source of liquid carbon dioxide 28 is also connected to storage tank 12 through valve 30 and heater 32.

Sterilizer tank 34 is connected to storage tank 12 both through compressor 40 for pumping the gas mixture into sterilizer tank 34 and through vacuum pump 50 for removing the gas mixture from sterilizer tank 34 into storage tank 12. The compressor 40 is also provided with a conventional gas cooler 42 and a compressor valve 44. Vacuum pump 50 is also provided with a gas cooler 52 and vacuum valves 54 and 58. It is also connected to air outlet vent 60 through flame guard 62 and air outlet valve 64. Sterilizer tank 34 is also provided with an air inlet vent 70 connected to it through valve 72 and an outlet valve 74. Storage tank 12 is also connected to the inlet of vacuum pump 50 through valve 46.

In order to initially fill storage tank 12 with a mixture of ethylene oxide and carbon dioxide, storage tank 12 is suitably evacuated by opening valves 46, 54 and 64 with all the other valves being closed. Vacuum pump 50 can then be operated to evacuate storage tank 12 through air outlet 60 to a suitably low value of 25 to 26 inches of mercury. Valves 46, 54 and 64 are then closed.

Scale 26 is then set to the desired quantity of ethylene oxide to open valve 24 and introduce a predetermined quantity of ethylene oxide from source 22 into storage tank 12, after which valve 24 automatically closes.

Carbon dioxide valve 30 is then opened to introduce carbon dioxide from source 28 into storage tank 12 through heater 32. Heater 32 is operated to heat the carbon dioxide to a temperature of about 200°–250° F., preferably 225° F., to prevent the condensation of ethylene oxide in storage tank 12 by reason of the cooling effect of the introduction of carbon dioxide which would otherwise occur. The introduction of carbon dioxide proceeds until the desired proportions of ethylene oxide and carbon dioxide are present, as indicated by gas analyser 20. The pressure in storage tank 12 should be about 30 to 40 pounds per square inch gauge. For effective sterilization, it is desirable that at least 10% ethylene oxide be present in the gas mixture in sterilizer tank 34 at all times, as indicated by the dashed line 10 of FIG. 2 and, to achieve this, it is preferred that somewhat higher percentages, say 12 to 15%, be present, although even higher percentages, perhaps up to 50%, may be used in certain circumstances. As shown in the ternary diagram of FIG. 2, the initial mixture of ethylene oxide and carbon dioxide is indicated at point A as between 10 and 15%.

The successive sterilizing cycles are then begun by sterilizing loads in succession in sterilizing tank 34, reusing the mixture by recirculating it to storage tank 12, while continuously maintaining it as a gas, and refortifying it by the addition of substantially pure ethylene oxide so that the proportion of ethylene oxide initially present in the mixture sterilizing each load is at least 10%. Since the mixture acquires a small amount of air during each sterilization cycle for which it is used, the refortification with ethylene oxide and the acquisition of air resulting in the mixture used for each successive load is characterized by a proportion at least 10% ethylene oxide, a decreasing proportion of carbon dioxide and an increasing proportion of air. This is apparent from FIG. 2, in which the proportion of air in the mixture increases along a line from point A to point B, generally in the manner as disclosed in the Satas patent.

According to the present invention, when, after a number of sterilization cycles which may be as high as 50 to 60, the increasing proportion of air in the mixture produces a mixture which approaches the region of flammability of the mixture, that is, on the FLAMMABLE side of line 11 of FIG. 2, which, with 10–15% ethylene oxide, amounts to about 50% air, a complete proportional fraction of the mixture is vented, the mixture of gases in the vented portion being in approximately the same proportions as in the entire mixture and in the unvented portion, so that the proportions of gases in the mixture before and after venting are the same. Thereafter, carbon dioxide is added to the mixture, thus increasing the proportion of carbon dioxide in the mixture to reduce the proportion of air by an amount which may be as small as 20%, while retaining the proportion of ethylene oxide in the mixture at least as great as 10%. As may be seen in FIG. 2, in a typical operation, although venting does not alter the proportions of the mixture from those shown at point B, increasing the proportion of carbon dioxide after venting changes the proportions of the mixture from those shown at point B to those shown at point C, with the entire mixture remaining in its gaseous condition at all times. Thus, by the use of the methods of the present invention, an indefinite number of successive loads may be sterilized without entering the region of flammability of the mixture and without the necessity of condensing any of the gases of the mixture in order to reduce the proportion of air.

Although it is important to maintain the proportion of air in the mixture at a low enough value so that it does not closely approach the region of flammability when present in the system including storage tank 12 and sterilizer tank 34, as measured by gas analyser 20, it has proved to be safe to vent a mixture while passing through the region of flammability during the venting procedure by using a suitable flame arrestor.

Referring again to FIG. 1, in a sterilization system for use with the present invention in which the sterilization and storage tanks both have a volume of about 750 cubic feet and the storage tank has been filled as described above, the following procedure is typical:

(1) The sterilizer tank 34 is heated to 155° F. and maintained at that temperature.

(2) A load to substantially fill the sterilizer tank 34 is placed inside and the sterilizer tank door is closed.

(3) A vacuum (25 to 26 inches of mercury) is created in sterilizer tank 34 through open valves 74, 54 and 64 using vacuum pump 50 and venting through flame guard 62 and air outlet 60. The other valves are closed. Valves 74, 54 and 64 are then closed and vacuum pump 50 is stopped.

(4) Valve 44 is then opened and compressor 40 operated to permit the gas mixture from storage tank 12 to build up a pressure of about 27 to 30 pounds per square inch gauge in sterilizer tank 34. Valve 44 is then closed and compressor 40 stopped. The load is left to sterilize.

(5) Valves 74, 54 and 58 are opened while the other valves are closed. The entire gas mixture is pumped from sterilizer tank 34 into storage tank 12 using vacuum pump 50 until a vacuum of 25 to 26 inches of mercury is obtained in sterilizer tank 34.

(6) Valves 74, 54 and 58 are closed and air is bled into sterilizer tank 34 through valve 72 and air inlet 70 until atmospheric pressure is attained.

(7) The sterilizer tank 34 is unloaded.

(8) Loss of ethylene oxide gas is determined by analysis of the gas mixture in storage tank 12 using gas analyser 20. The proportion of air is also measured.

(9) Liquid ethylene oxide is added to storage tank 12 from source 22 through valve 24 until the proportion of ethylene oxide shown by analyser 20 is at least 10% and preferably 12 to 15%.

(10) Repeat steps 2 to 9 for several cycles (which may be as high as 50 to 60) until the proportion of air is short of about 50%, as shown by gas analyser 20. Typically this might occur at point B in the ternary diagram of FIG. 2, at which point the approximate proportions of the gas mixture are: ethylene oxide 15%; carbon dioxide 46% and air 38%.

(11) Vent a portion of the gas mixture from storage tank 12 through flame guard 16 and mixture vent 14 by opening valve 18, in an amount to maintain the ethylene oxide in a proportion of at least 10% after dilution.

This typically will result in reducing the pressure in storage tank 12 from about 30 to 40 pounds per square inch gauge to about 15 to 25 pounds per square inch gauge.

Since the proportions of gases in the vented portion of the mixture and in the remaining unvented portion of the mixture are the same, the composition of the mixture will remain at point B of FIG. 2 during venting.

(12) Add carbon dioxide to the remaining unvented gas mixture in an amount sufficient to raise the pressure in storage tank 12 about back to its original value of 30 to 40 pounds per square inch gauge. This typically might result in establishing the mixture at point C in the ternary diagram of FIG. 2, at which point the approximate proportions of the gas mixture are: ethylene oxide 12%; carbon dioxide 58% and air 29%.

(13) Repeat the steps (2) through (12) an indefinite number of times without the venting of the entire gas mixture from the system.

While the preferred inert gas used in the method of this invention is carbon dioxide, other inert gases, particularly nitrogen, may be used as well.

What is claimed is:

1. A method of sterilization an indefinite number of successive loads to be sterilized with a nonflammable gas mixture containing at least 10 percent ethylene oxide gas and an inert gas selected from the group consisting of carbon dioxide and nitrogen, comprising the steps of:

sterilizing said successive loads in individual sterilization cycles in succession in a sterilizing tank by reusing said mixture by recirculating it to a storage tank after each sterilization cycle while continuously maintaining it as a gas and refortifying it by the addition of substantially pure ethylene oxide so that the proportion of ethylene oxide initially present in the mixture sterilizing each load for each sterilization cycle is at least 10%, said mixture acquiring a small amount of air during each sterilization cycle for which it is used, said refortification with ethylene oxide and said acquisition of air resulting in the mixture used for each successive sterilization cycle being characterized by a proportion of at least 10% ethylene oxide, a decreasing proportion of inert gas and an increasing proportion of air, periodically venting only a fraction of said mixture when the increasing proportion of air in said mixture produces a mixture which approaches the region of flammability of said mixture and increasing the proportion of inert gas in said mixture to reduce the proportion of air in said mixture while retaining the proportion of ethylene oxide in said mixture at least as great as 10% and thereafter continuing sterilizing said loads in individual sterilization cycles in succession in said sterilizing tank by reusing said mixture by recirculating it to said storage tank after each sterilization cycle while continuously maintaining it as a gas and refortifying it by the addition of substantially pure ethylene oxide so that the proportion of ethylene oxide initially present in the mixture sterilizing each load for each sterilization cycle is at least 10% until the proportion of air in said mixture again approaches the region of flammability.

2. In a method as claimed in claim 1, wherein after said venting, the proportion of air in said mixture is maintained between about 20% and 50%.

3. In a method as claimed in claim 2, wherein said inert gas is carbon dioxide.

* * * * *